United States Patent [19]
von Torklus et al.

[11] Patent Number: 4,532,921
[45] Date of Patent: Aug. 6, 1985

[54] KNEE JOINT BANDAGE

[76] Inventors: Detlef von Torklus, Jungfrauenthal 20; Oskar Thum, Bebelallee 116; Friedrich Wilharm, Martinistrasse, all of Hamburg, Fed. Rep. of Germany

[21] Appl. No.: 261,711

[22] Filed: May 8, 1981

[51] Int. Cl.³ .............................................. A61F 5/00
[52] U.S. Cl. .................................. 128/80 C; 128/165
[58] Field of Search ................ 128/75, 80 R, 80 C, 128/84 R, 87 R, 89 R, 132 R, 133, 157, 165; 2/24

[56] References Cited

U.S. PATENT DOCUMENTS

| | | | |
|---|---|---|---|
| 1,637,116 | 7/1927 | Kelley | 2/24 |
| 2,641,761 | 6/1953 | Schultz | 128/157 X |
| 2,858,540 | 11/1958 | Morrison | 128/80 C |
| 3,194,233 | 7/1965 | Peckham | 128/165 X |
| 3,318,305 | 5/1967 | Schultz | 128/80 R |
| 3,786,804 | 1/1974 | Lewis | 128/80 C |
| 3,934,583 | 1/1976 | Hollingshead et al. | 128/80 C X |
| 3,945,046 | 3/1976 | Stromgren | 128/80 C X |
| 3,970,081 | 7/1976 | Applegate, Jr. | 128/165 X |
| 4,240,414 | 12/1980 | Theisler | 128/80 C |
| 4,275,716 | 6/1981 | Scott, Jr. | 128/80 C |
| 4,296,744 | 10/1981 | Palumbo | 128/165 X |

Primary Examiner—Lee S. Cohen
Assistant Examiner—Angela D. Sykes
Attorney, Agent, or Firm—Michael J. Striker

[57] ABSTRACT

A knee joint bandage has a downwardly decreasing knee hose element composed of an elastic material and having a front side and a central region of its height, and a supporting element connectable with the hose element at the front side and in the central region of the height of the hose element and having a central supporting portion which is bent downwardly in correspondence with the user's knee disk so that upon putting the bandage on the user's leg the supporting portion abuts against the user's knee disk from below and thereby supports the user's knee disk from below.

12 Claims, 4 Drawing Figures

KNEE JOINT BANDAGE

BACKGROUND OF THE INVENTION

The invention relates to a knee joint bandage with a conically downwardly decreasing knee hose of an elastic material, such as a rubber fabric tube, which in practice is identified as so-called knee cap. With the aid of such a bandage, an unloading of sick gliding face of the knee disk (patella) is provided. In this case malformations can take place such as generally deterioration or gristle loosening. When a smooth gliding face is no longer available because of a deformity, the movement of the knee and particularly of the knee disk causes pain.

SUMMARY OF THE INVENTION

The object of the invention is to provide a knee joint bandage with which the knee disk is unloaded during working and generally during movement of the knee, to a greater extent than was possible in the known means, so as to attain thereby a relief of the ailments in the event of the above-mentioned sicknesses and a complete cure in early cases. In accordance with the invention it is provided therefor that the knee hose has at its front side a holder extending transversely approximately in middle height and carrying a supporting strap which supports the knee disk at its lower side. Thereby, the supporting strap can be inserted into a cavity or in a depression between the lower terminal of the knee disk and the shin bone snag over the knee disk band and support the knee disk from below to a lifted position and during a movement of the knee joint hold the knee disk in the lifted position.

Thereby a pressure is accurately applied to the knee disk band. Because of such lifting of the knee disk, the knee disk in its upper region is raised from the knee joint, and thereby the friction in the region of the gliding face is reduced. The knee hose thus takes care for the remaining position of the supporting strap. The supporting strap can therefore be built in the knee bone. It is, however, advantageous when the holder is formed as a tubular guide through which the supporting strap extends, whereas the holder is composed advantageous of the same material of which the hose is composed, so that for washing of the knee hose the supporting strap can be removed from the guide.

The supporting strap is advantageously bulge shaped in its supporting portion, that is in its middle portion. It can be composed, for example, of a jacket which is provided with a filling, for example of felt or another flexible material.

The end portions of the supporting strap are provided with connecting means, for example with a burdock band connection, so that the strap can be applied in different lengths and be suitable for wearing by persons with different calf diameters. In order to guarantee a fixed position, the end portions are composed advantageously of an extensible material. For example they are composed of a rubber band.

It has been shown to be useful when the end portions of the supporting strap are inclined downwardly relative to the supporting portion, and thereby the supporting strap does not abut against the knee throat, but is located below the latter and thereby does not hinder the walking movement.

The supporting portion of the supporting strap proper can be bent downwardly so as to provide for greater adaptability to the downwardly curved knee disk and thereby a wider abutment.

DESCRIPTION OF THE DRAWINGS

An exemplified embodiment of the invention is illustrated hereinbelow with references to a drawing. The drawing shows.

DESCRIPTION OF A PREFERRED EMBODIMENT

Figure 1:
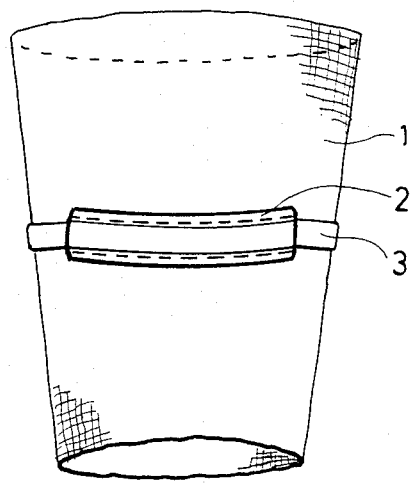
FIG. 1: a knee joint bandage in the plan view.
Figure 2:
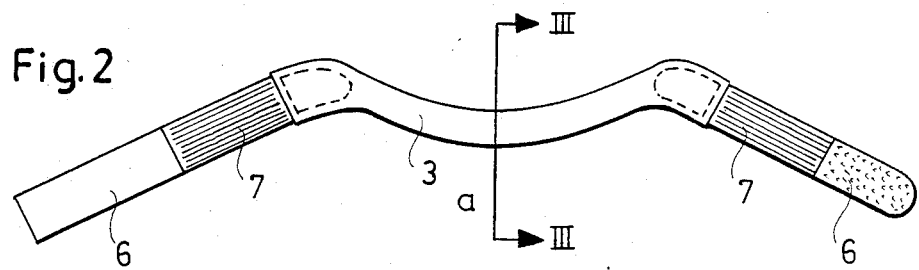
FIG. 2: the supporting strap in the plan view.
Figure 3:
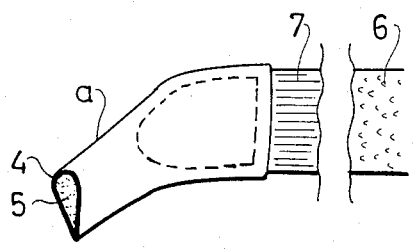
FIG. 3: the supporting portion of the supporting strap in transverse section.

The drawing shows in FIG. 1 a knee joint bandage with a known knee hose 1 which is composed of an elastic fabric, such as a rubber fabric, and thereby is stretchable in all directions. The tubular knee hose 1 is formed so that it conically decreases downwardly so as to take into consideration the fact that the upper leg part has generally a greater diameter than the lower leg part.

A holder 2 formed as a tubular guide is sewn on the knee hose 1 and advantageously is composed of the same material of which the knee hose 1 is composed. It may, however, be composed for example of leather. A supporting strap 3 extends through this holder 2 and is downwardly curved in its middle supporting portion a. The middle portion a is overlapped by the guide 2. It is composed of a leather jacket 4 which is sewn together at its lower side and surrounds a filling 5 of felt or another material. The jacket 4 may, however, be also composed of the same material of which the knee hose 1 is composed. The middle portion a is curved downwardly in correspondence with the tubular holder 2, in order to provide a maximum possible wide support.

The end portions of the supporting strap 3 are designed as burdock band connectors 6 which is known per se in the art. The supporting strap 3 is provided with stretchable portions 7 between the end portions and the middle supporting portion a, the portions 7 being formed as rubber bands in order to make possible adaptation of the supporting strap in the sense of its active length to the respective requirements.

Figure 4:
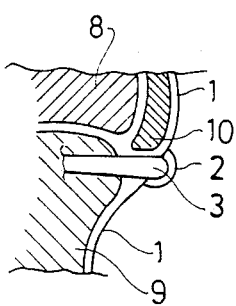
FIG. 4: a schematic reproduction of the knee joint with the applied knee joint bandage.

In use of the knee joint bandage, the knee hose 1 is pulled through the foot and the lower leg part upwardly to such an extent that the supporting strap 3 lies in a groove shaped cavity below the knee disk 10 of FIG. 4. The knee hose 1 covers thereby the upper portion of the lower leg bone 9 (tibia) and the lower portion of the upper leg bone 8 (femur). During a movement, the knee disk 10 is retained by the supporting strap 3 in the lifted position. Thereby an unloading is continuously attained.

It will be understood that each of the elements described above, or two or more together, may also find a useful application in other types of constructions differing from the types described above.

While the invention has been illustrated and described as embodied in a knee joint bandage, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A knee joint bandage, comprising a downwardly decreasing knee hose element composed of an elastic material and having a front side and a central region of its height; a supporting element connectable with said hose element at said front side and in said central region of the height of said hose element, said supporting element having a central supporting portion which is bent downwardly in correspondence with the user's knee disk so that upon putting the bandage on the user's leg said supporting portion abuts against the user's knee disk from below and thereby supports the user's knee disk from below; and means for connecting said supporting element with said hose element to effect support of the user's disk from below.

2. A knee joint bandage as defined in claim 1, wherein said supporting element is formed as a supporting strap extending transversely of said knee hose element.

3. A knee joint bandage as defined in claim 1, wherein said connecting means includes a holding element arranged on said front side and in the central region of the height of said knee hose element and extending transversely of the latter, said supporting element being connected with said knee hose element by said holding element.

4. A knee joint bandage as defined in claim 3, wherein said holding element is formed as a tubular guide through which said supporting element extends.

5. A knee joint bandage as defined in claim 3, wherein said holding element and said knee hose element are composed of the same material.

6. A knee joint bandage as defined in claim 1, wherein said supporting element is composed of a jacket with a filling accommodated in the latter.

7. A knee joint bandage as defined in claim 1, wherein said supporting element has two ends connectable with one another; and further comprising connecting means for connecting said ends with one another and including a burdock band connection.

8. A knee joint bandage as defined in claim 6, wherein said supporting element includes two end portions which are wider than said central supporting portion.

9. A knee joint bandage as defined in claim 1, wherein said supporting element has outer portions surrounding said central supporting portion, said outer portions of said supporting element being inclined downwardly at a predetermined angle.

10. A knee joint bandage as defined in claim 1, wherein said supporting element has two end portions connectable with one another, and two stretchable portions each located between said central supporting portion and a respective one of said end portions.

11. A knee joint bandage as defined in claim 1, wherein said central supporting portion of said supporting element is formed so that upon putting of the bandage onto the user's leg said supporting portion is inserted into the cavity formed between the lower terminal of the knee disk and the shin bone snag over the knee disk band, to support the knee disk from below in a lifted position.

12. A knee joint bandage as defined in claim 1, wherein said supporting element has at least one portion composed of a stretchable material.

* * * * *